US009539346B1

(12) United States Patent
Larsen et al.

(10) Patent No.: US 9,539,346 B1
(45) Date of Patent: Jan. 10, 2017

(54) RADIOTHERAPEUTIC PARTICLES AND SUSPENSIONS

(71) Applicant: Oncoinvent AS, Oslo (NO)

(72) Inventors: Roy Hartvig Larsen, Oslo (NO); Sara Westrøm, Oslo (NO)

(73) Assignee: Oncoinvent AS (NO)

( * ) Notice: Subject to any disclaimer, the term of this patent is extended or adjusted under 35 U.S.C. 154(b) by 0 days.

(21) Appl. No.: 14/798,258

(22) Filed: Jul. 13, 2015

Related U.S. Application Data

(63) Continuation of application No. 14/791,313, filed on Jul. 3, 2015.

(30) Foreign Application Priority Data

Jul. 3, 2015 (EP) .................... 15175318

(51) Int. Cl.
*A61K 51/02* (2006.01)
*A61K 51/12* (2006.01)
*A61K 51/10* (2006.01)
*C01F 11/18* (2006.01)

(52) U.S. Cl.
CPC ......... *A61K 51/025* (2013.01); *A61K 51/1093* (2013.01); *A61K 51/1244* (2013.01); *C01F 11/18* (2013.01); *C01P 2004/64* (2013.01); *C01P 2006/44* (2013.01)

(58) Field of Classification Search
CPC ........... A61K 9/14; A61K 51/00; A61K 51/12
See application file for complete search history.

(56) References Cited

U.S. PATENT DOCUMENTS

| 4,970,062 | A | 11/1990 | Atcher et al. | |
| 6,455,024 | B1* | 9/2002 | Glajch | A61K 51/1251 424/1.25 |
| 8,142,758 | B2* | 3/2012 | Larsen | A61K 51/1244 424/1.29 |
| 2009/0246285 | A1* | 10/2009 | Stellacci | A61K 9/5123 424/490 |

FOREIGN PATENT DOCUMENTS

| EP | 1812115 A2 | 8/2007 |
| WO | 99/51278 A1 | 10/1999 |
| WO | 2012/131378 A2 | 10/2012 |

OTHER PUBLICATIONS

Roy H. Larsen et al., 211At-labelling of polymer particles for radiotherapy: Synthesis, purification and stability, Journal of Labelled COmpounds and Radiopharmaceuticals, vol., XXXIII (10), 977-986, 1993.*
Bloomer et al., "Astatine-211—Tellurium Radiocolloid Cures Experimental Malignant Ascites", Science, vol. 212, Apr. 17, 1981, pp. 340-341.
Boudousq et al., "Comparison between Internalizing Anti-HER2 mAbs and Non-Internalizing Anti-CEA mAbs in Alpha-Radioimmunotherapy of Small Volume Peritoneal Carcinomatosis using 212Pb", PLoS, vol. 8, No. 7, Jul. 29, 2013, pp. 1-14.
Gerber et al., "Preferential Attachment of Peritoneal Tumor Metastases to Omental Immune Aggregates and Possible Role of a Unique Vascular Microenvironment in Metastatic Survival and Growth", The American Journal of Pathology, vol. 169, No. 5, Nov. 2006, pp. 1739-1752.
Gustafsson et al., "Comparison of Therapeutic Efficacy and Biodistribution of 213bi- and 211At-labeled Monoclonal Antibody MX35 in an Ovarian Cancer Model", Nuclear Medicine and Biology, vol. 39, 2012, pp. 15-22.
Kirby et al., "The Radiochemistry of Radium", National Academies Press, Dec. 1964, pp. 1-205.
Liu, Shuang, "Bifunctional Coupling Agents for Radiolabeling of Biomolecules and Target-specific Delivery of Metallic Radionuclides", Advanced Drug Delivery Reviews, vol. 60, No. 12, Sep. 2008, pp. 1347-1370.
Ritter et al., "High-LET Radiations Induce a Large Proportion of Nonrejoining DNA Breaks", Nature, Apr. 14, 1977, vol. 266, No. 5603, pp. 653-655.
Vergote et al., "Therapeutic Efficacy of the α-Emitter 211 At Bound on Microspheres Compared With 90Y and 32P Colloids in a Murine Intraperitoneal Tumor Model", Gynecologic Oncology, vol. 47, 1992, pp. 366-372.
Extended European Search Report received for European Patent Application No. 15175318, issued on Dec. 10, 2015, 3 pages.
Voltaggio et al., "Implantation of Recoiling Radionuclides of U and Th Radioactive Series Applied to Estimation of Surficial Erosion of CaCO3 Materials", Applied Geochemistry, vol. 16, 2001, pp. 835-848.

* cited by examiner

*Primary Examiner* — Michael G Hartley
*Assistant Examiner* — Jagadishwar Samala
(74) *Attorney, Agent, or Firm* — Morrison & Foerster LLP

(57) ABSTRACT

The present invention relates to a particle or pharmaceutical composition comprising one, more particles or a suspension of same or different particles comprising a degradable compound and an alpha emitting radionuclide and/or a radionuclide generating alpha emitting daughter. The particles are beneficial for use in the treatment of cancer.

11 Claims, 3 Drawing Sheets

RADIOTHERAPEUTIC PARTICLES AND SUSPENSIONS

CROSS-REFERENCE TO RELATED APPLICATIONS

This application is a continuation of U.S. patent application Ser. No. 14/791,313, filed Jul. 3, 2015, and claims foreign priority to European Patent Application No. 15175318.3, filed Jul. 3, 2015, which are incorporated herein by reference in their entireties.

FIELD OF THE INVENTION

The present invention relates to a particle or pharmaceutical composition comprising one or more particles or a suspension of same or different particles comprising a degradable compound and an alpha emitting radionuclide and/or a radionuclide generating alpha emitting daughter. The particles are beneficial for use in the treatment of cancer.

BACKGROUND OF THE INVENTION

Beta-emitting radiocolloids and microparticles were used for several years with some success against peritoneal ascites and microscopic tumor seeds. However, late effects and morbidity due to intestinal toxicity have made these treatments obsolete and chemotherapy has become the standard adjuvant therapy in e.g. ovarian cancer.

There still exists a considerable medical need for new modalities against intracavitary cancer.

Alpha emitters have previously been proposed as a treatment for intraperitoneal cancer. Two types of chemical classes have been proposed, (1) radioimmunoconjugates and (2) micro- or nano-sized particular suspensions. The advantage with the radioimmunoconjugates is the potential for cell specific targeting and the disadvantage is the substantial leakage of product into the bloodstream causing potential systemic toxicity.

The advantage with micro/nano particles and colloids is the potential for improved local retention reducing distant toxicity. On the down side is the potential for in-homogenous dose deposition and radiation hot spots and also whether the particle itself can cause irritation because of inertness to degradation etc.

If microparticles and/or nanoparticles are to be used the choice is if they should be completely stable or slowly degradable.

By using completely stable particles the advantages include low risk of systemic toxicity. Disadvantages include potentially more heterogenous radiation dose distribution and some risk of local toxicity from "hot spots". Stable radiotherapeutic particles have been used for radioembolization using the high energetic beta emitter $^{90}$Y stably labeled to non-degradable glass spheres (TheraSphere™) or resin based spheres (SIR-Spheres™) for treating primary tumors and metastases to the liver. The liver tissue will in this instance shield against toxic radiation to intestines etc.

A second approach would be to use degradable particles slowly releasing some of the radionuclides: Possible advantages includes a more homogenous radiation dose distribution due to improved diffusion of mother nuclides and or short lived daughter nuclides and less tendency for "hot spots" causing local toxicity. Possible disadvantages include potential for systemic toxicity due to possible transport of released radionuclide into the blood and further redistribution. Degradable particles are mostly used for other cytotoxic compounds like chemotherapeutics and not for radionuclides at the moment.

Thus there is a need for an improved delivery system for alpha particle radiation against intracavitary cancers.

SUMMARY OF THE INVENTION

An object of the present invention relates to a particle comprising a degradable compound and an alpha emitting radionuclide and/or a radionuclide generating alpha emitting daughter.

In one embodiment of the present invention is the radionuclide selected from the group consisting of $^{224}$Ra, $^{212}$Bi, $^{212}$Pb $^{223}$Ra, $^{225}$Ra, $^{225}$Ac, $^{213}$Bi, $^{211}$At, $^{227}$Th.

In another embodiment of the present invention is the degradable compound selected from the group consisting of $CaCO_3$, PEG modified $CaCO_3$ protein modified $CaCO_3$, carbohydrate modified $CaCO_3$, lipid modified $CaCO_3$, vitamin modified $CaCO_3$, organic compound modified $CaCO_3$, polymer modified $CaCO_3$ and/or inorganic crystal modified $CaCO_3$.

In a further embodiment of the present invention is the size of the particle from 1 nm to 500 μm.

In another embodiment of the present invention, the particle comprises one or more compounds selected from the group consisting of a monoclonal antibody, a polyclonal antibody, a radioimmunoconjugate, an immunoconjugate, a chelate antibody conjugate, vitamins including folate and folate derivatives, peptides, minibodies, and affibodies.

In a further aspect of the present invention relates to a pharmaceutical composition comprising one or more particles according to the invention and a diluent, carrier, surfactant, and/or excipient.

In another embodiment of the present invention is the pharmaceutical composition prepared with an amount of radionuclide that is 1 kBq to 10 GBq per dosing.

In another embodiment of the present invention is the pharmaceutical composition prepared with an amount of radionuclide that is 50 MBq to 100 GBq suitable for multidose industrial scale production.

In another embodiment of the present invention is the pharmaceutical composition a particle suspension comprising monodisperse or polydisperse particles labeled with an alpha emitting radionuclide and/or a radionuclide generating alpha emitting daughter.

In another embodiment of the present invention is the pharmaceutical composition suitable for intravenous or intracavitary injection.

Another aspect of the present invention relates to a particle or pharmaceutical composition of the present invention for use as a medicament.

A further aspect of the present invention relates to a particle or pharmaceutical composition of the present invention for use in intracavitary therapy, radioembolization or radiosynovectomy.

Another aspect of the present invention relates to a particle or pharmaceutical composition of the present invention for use in the treatment of cancer.

In one embodiment of the present invention is the cancer selected from the group consisting of intraperitonial cancers, intracranial cancers, pleural cancers, bladder cancers, cardiac cancers, and cancers in the subarachnoid cavity.

Another aspect of the present invention relates to a method of treatment or amelioration comprising administration of the particles or the pharmaceutical composition of the present invention to an individual in need thereof.

Another aspect of the present invention relates to a method for preparing a particle of the present invention, the method comprising bringing an alpha emitting radionuclide and a biodegradable compound in contact with each other with or without using a carrier for the radionuclide.

Another aspect of the present invention relates to a kit comprising a nano or micro particle according to the present invention, an alpha emitting radionuclide or a radionuclide generating an alpha emitting daughter, a carrier, diluent and/or excipient, and optionally instructions to use the kit.

Another aspect of the present invention relates to a kit comprising a nano or micro particles according to the present invention, an alpha emitting radionuclide or a radionuclide generating an alpha emitting daughter, a carrier, diluent and/or excipient, and optionally instructions to use the kit to prepare a bifunctional pharmaceutical solution comprising particles suspension and radioimmunoconjugate solution.

In one embodiment of the present invention, the kit comprises a chelator-conjugated molecule, including monoclonal antibody.

DETAILED DESCRIPTION OF THE INVENTION

Figure 1A:
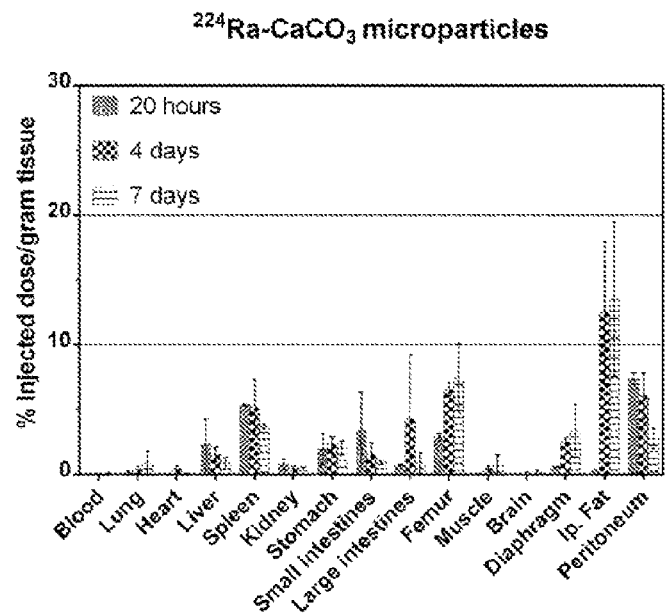
FIGS. 1A and 1B show tissue distribution 20 hours, 4 days and 7 days after intraperitoneal injection of $^{224}$Ra-labeled CaCO$_3$ microparticles (FIG. 1A) and dissolved $^{224}$RaCl$_2$ (FIG. 1B) in nude mice. The radioactivity measurements are performed minimum 3 days after sacrificing the animals, i.e. allowing time for daughter nuclides to be in equilibrium with $^{224}$Ra.

The present inventors have identified a treatment of cancer with less risk for intestinal toxicity based on short ranging alpha emitters.

The current invention is based on slowly degradable nano- or microparticles comprising an alpha emitting radionuclide and/or a radionuclide generating alpha emitting daughter, e.g. $^{224}$Ra.

Thus, one object of the present invention relates to a particle comprising a degradable compound and an alpha emitting radionuclide and/or a radionuclide generating alpha emitting daughter.

Radionuclides

The radionuclides of the present invention can be any alpha emitting radionuclide and/or a radionuclide generating alpha emitting daughter.

The main advantages of alpha particle emitting compounds in local therapy in e.g., the intraperitoneal cavity is the shorter range, typically less than 0.1 mm for alphas compared with mm to cm ranges for beta-particles from medical beta emitters like $^{90}$Y, $^{131}$I and $^{32}$P.

Use of alpha-emitters would in an intracavitary setting reduce risk for toxicity due to irradiation of deeper regions of internal organs like the radiosensitive intestinal crypt cells in the case of i.p. use. Also is the high linear energy transfer of the emitted alpha particles advantageous since very few alpha hits are needed to kill a cell and cellular resistance mechanism like high repair capacity for DNA strand breaks is less of a problem because of the high probability of producing irreparable double strand breaks (Ritter et al., 1977).

The high effect per decay means less radioactivity is needed reducing the need for shielding of hospital staff and relatives since most alpha- and beta emitters also emits some X-rays and gammas which needs to be shielded against.

Table 1 shows the main radiation properties of $^{224}$Ra. The complete decay of $^{224}$Ra and daughters produce in total 4 alpha-particles. An important aspect is the fate of the $^{220}$Rn as this nuclide potentially could diffuse away from the mother nuclide as it is potentially chemical inert to bonding in crystals.

TABLE 1

Main radiation properties from the $^{224}$Ra series.

| Radionuclide (half life) | Alphas and betas (mean energy in MeV) | X-rays and gammas Energy and % abundance |
|---|---|---|
| $^{224}$Ra (3.6 days) | αa (3.6 | 241 keV, 4.1% |
| $^{220}$Rn (55.6 s) | αn (55. | |
| $^{216}$Po (145 ms) | αo (14 | |
| $^{212}$Pb (10.6 h) | βb (10 | 75 keV, 10.3% |
| | | 77 keV, 17.1% |
| | | 87 keV, 6.0% |
| | | 90 keV, 1.5% |
| | | 239 keV, 43.6% |
| | | 300 keV, 3.3% |
| $^{212}$Bi (1.0 h) | αi (1.0 h).3%% bundance energy$^1$) βi (1.0 h).3%% bundance energy | 727 keV, 6.7% (4.3% effective) |
| $^{212}$Po (299 ns) (64% branch) | α64% branch)% (4.3% ef | |
| $^{208}$Tl (3.1 min) (36% branch) | β36% branch)% (4.3% ef | 75 keV, 3.4% (1.2% effective) |
| | | 511 keV, 22.6% (8.1% effective) |
| | | 583 keV, 85.0% (30.6% effective) |
| | | 860 keV, 12.5% (4.5% effective) |
| | | 2615 keV, 99.8% (35.9% effective) |

$^1$Average per $^{224}$Ra transformation due to branching. Only X-rays or gammas above 1% effective abundance accounted for. Adds up to a total effective energy of approximately 26.5 MeV of alpha of 0.7 MeV of beta per complete decay of $^{224}$Ra and daughters.

Radium-224 is one alpha-emitter, but others can also be applied to the present invention.

Thus, in one embodiment of the present invention is the radionuclide selected from the group consisting of $^{224}$Ra $^{212}$Bi, $^{212}$Pb $^{223}$Ra, $^{225}$Ra, $^{225}$Ac, $^{213}$Bi, $^{211}$At, $^{227}$Th.

A very advantageous finding in the examples was that the amount of radioactivity needed for producing significant therapeutic effects was as low as 200 kBq per kg of body weight which is equivalent with only 4-5 kBq per mouse. This compares favorably to the several hundred kBq per mouse of $^{211}$At and $^{212}$Pb needed in alpha-radioimmunotherapy against experimental peritoneal cancer in mice (Gustafsson et al., 2012; Boudousq et al., 2013). This property could strongly reduce exposure problems from X-rays and gammas during administration and use of the particles of the present invention, exemplified by $^{224}$Ra-CC.

The amount of $^{224}$Ra used per patient dosage may be in the range of 1 kBq to 10 GBq more preferably 100 kBq to 100 MBq, event more preferably range is 0.5 MBq to 25 MBq.

In one embodiment of the present invention is the pharmaceutical composition prepared with an amount of radionuclide that is 1 kBq to 10 GBq per dosing.

In another embodiment of the present invention is the pharmaceutical composition prepared with an amount of radionuclide that is suitable for multidose industrial scale production e.g., 50 MBq to 100 GBq.

Degradable Compound

The degradable compound of the present invention can be any compound that can be degraded.

The degradation can be done by any route selected from the group consisting of high pH, low pH, proteases, enzymes, nucleases and/or by cellular processes like endocytosis, which also includes phagocytosis.

In one embodiment of the present invention is the degradable compound selected from the group consisting of $CaCO_3$, PEG modified $CaCO_3$ protein modified $CaCO_3$, carbohydrate modified $CaCO_3$, lipid modified $CaCO_3$, vitamin modified $CaCO_3$, organic compound modified $CaCO_3$, polymer modified $CaCO_3$ and/or inorganic crystal modified $CaCO_3$ In a preferred embodiment of the present invention is the degradable compound $CaCO_3$ (CC).

Calcium carbonate (CC) particles may be used as composites with other salts or proteins or peptides and subject to surface modification by surfactants like oleates and similar.

In a special embodiment is CC used with a compound selected from the group consisting of poly ethylene glycol modified particles of calcium carbonate or inorganic crystal modified CC.

In a special embodiment the CC particles is modified with functional receptor and or antigen binding groups, including monoclonal antibodies and derivatives and vitamins and derivatives allowing receptor or antigen binding of particle to individual target cells and diseased tissues.

When $^{224}Ra$ solution in equilibrium with daughter nuclides is used for labeling of particles a special embodiment is to firstly add to the solution a chelator for $^{212}Pb$ before contacting CC particles, thus creating a bifunctional radiotherapeutic mixture. The chelator is preferentially conjugated to a target affinic molecule, e.g., monoclonal or polyclonal antibody or derivatives of antibody, vitamins or derivatives of vitamins.

Characteristics

The particles can have a variety of characteristics.

The size of the particles can vary depending on the intended uses and applications.

The type of crystals may be any known form of CC and sizes varying from 1 nm to 500 µm may be used. More preferentially the size is in the range of 100 nm to 50 µm and further preferentially is size in the range of 1-10 µm.

In one embodiment of the present invention is the size of the particle from 1 nm to 500 µm.

In mice, based on the peritoneal surfaces the amount of CC-particles should be in the range of 0.1 mg to 50 mg more beneficial probably 1 mg to 15 mg. In humans the amounts used should be multiplied by 10 to 10 000 compared with mice probably more beneficial with 0.1-10 g for e.g., intraperitoneal therapy. For other cavities the amounts may be adjusted according to relative surface area or to the volume of fluid present.

In the examples of the current invention it was found that $^{224}Ra$ could be used for radiolabeling of degradable calcium carbonate. Calcium carbonate has about 14% lower density that calcium hydroxyapatite and may be easier to keep in suspension without sedimenting vs. calcium hydroxyapatite particles of same size. Calcium carbonate was used as main ingredient with or without the addition of small amounts of co-precipitate e.g., barium sulphate, as carrier for the $^{224}Ra$.

Thus, in one embodiment are co-precipitate added. These are selected from the group consisting of barium sulphate, strontium sulphate, and barium chromate. The amount ranging typically from 0.01% to 10% vs. calcium carbonate, and preferably 0.1-1% vs. calcium carbonate.

Additional Compounds in the Particle

The degradable particle can comprise many different additional compounds. These can serve various purposes included targeting, stability, solubility and rate of degradation.

In one embodiment of the present invention, the particle comprises one or more compounds selected from the group consisting of a monoclonal antibody, a polyclonal antibody, a radioimmunoconjugate, an immunoconjugate, a chelate antibody conjugate, vitamins including folate and folate derivatives, peptides, minibodies, and affibodies.

In a special embodiment a pharmaceutical suspension of $^{224}Ra$-labeled includes a $^{212}Pb$-labeled antibody, antibody fragment or protein or peptide or vitamin derivative (targeting conjugate) with affinity for receptors including antigens on the tumor cells whereby the $^{224}Ra$-labeled particles will give a general alpha particle radiation field on the intraperitoneal surfaces including on the surfaces of intraperitoneal organs, and the $^{212}Pb$ labeled antibody or similar gives a specific alpha particle dose to the tumor cells by reseptor or antigen binding.

The radionuclides in the present invention can be conjugated to a targeting molecule by using bifunctional chelators.

These could be cyclic, linear or branched chelators. Particular reference may be made to the polyaminopolyacid chelators which comprise a linear, cyclic or branched polyazaalkane backbone with acidic (e.g. carboxyalkyi) groups attached at backbone nitrogens.

Examples of suitable chelators include DOTA derivatives such as p-isothiocyanatobenzyl-1,4,7,10-tetraazacyclododecane-1,4,7,10-tetraacetic acid (p-SCN-Bz-DOTA) and the tetra primary amide variant of this DOTA compound, termed TCMC, and DTPA derivatives such as p-isothiocyanatobenzyl-diethylenetriaminepenta-acetic acid (p-SCN-Bz-DTPA), the first being cyclic chelators, the latter linear chelators.

Metallation of the complexing moiety may be performed before or after conjugation of the complexing moiety to the targeting moiety.

The radiolabeling procedure will in general be more convenient in terms of time used etc if the chelator is conjugated to the antibody before the radiolabeling takes place.

The principles of preparing radiolabeled conjugates using chelators attached to antibodies are described broader in e.g. Liu, 2008.

Pharmaceutical Composition

In a further aspect of the present invention relates to a pharmaceutical composition comprising one or more particles according to the invention and a diluent, carrier, surfactant, and/or excipient.

Acceptable pharmaceutical carriers include but are not limited to non-toxic buffers, fillers, isotonic solutions, solvents and co-solvents, anti-microbial preservatives, anti oxidants, wetting agents, antifoaming agents and thickening agents etc. More specifically, the pharmaceutical carrier can be but are not limited to normal saline (0.9%), half-normal saline, Ringer's lactate, dissolved sucrose, dextrose, e.g. 3.3% Dextrose/0.3% Saline. The physiologically acceptable carrier can contain a radiolytic stabilizer, e.g. ascorbic acid, human serum albumin, which protect the integrity of the radiopharmaceutical during storage and shipment.

The pharmaceutical compositions can comprise a multitude of particles. These can be the same of different.

Thus, in another embodiment of the present invention is the pharmaceutical composition a particle suspension comprising monodisperse or polydisperse particles labeled with an alpha emitting radionuclide and/or a radionuclide generating alpha emitting daughter.

Administration

In another embodiment of the present invention is the pharmaceutical composition suitable for intravenous or intracavitary injection.

Applications

The use of alpha emitting microparticles against i.p. cancers has been suggested previously. Archer et al (U.S. Pat. No. 4,970,062 A) suggested to use ferric hydroxide colloid as carrier for alpha emitters, with emphasis of $^{212}$Pb but listing several other potential useful alpha-emitters including $^{224}$Ra. Bloomer et al (1981) suggested to use $^{211}$At labeled tellurium colloid, while Vergote et al (1992) suggested to use $^{211}$At-labeled monodisperse polymer particles. Larsen and Salberg (U.S. Pat. No. 8,142,758 B2) suggested to use hydroxyapatite particles labeled with $^{223}$Ra or other alpha emitters, including $^{224}$Ra. A problem with these are in the case of Archer et al., that hydroxide may not be a good for preparing radium labeled particle sine hydroxide of alkaline earth and particularly radium has a relatively high solubility in water (Kirby et al., 1964).

Astatine-211 tellurium colloid was found to be unstable causing exposure to thyroidea (Vergote et al., 1992) and that $^{211}$At-labeled polymer particles are not biodegradable and because of short half life and limited existing production capacity for $^{211}$At would be expensive and impractical in large scale clinical use. Also because of the chemical inertness and low complexability of cationic radium the use of tellurium colloids or polymer particles was not considered as carrier for radium. The use of hydroxyapatite as carrier for radium gives a good labeling yield but the calcium hydroxyapatite has a high density which could cause a more rapid sedimentation and less ideal dose distribution of the radiation when used in cavitary therapy as microparticular suspension.

The testing and research related to the novel particles, exemplified by $^{224}$Ra-labeled calcium carbonate (CC) particles presented herein had some unexpected findings: It was possible to obtain high labeling yield and relevant stability of the product in vitro, i.p. retention compatible with $^{224}$Ra half life, slow release of $^{224}$Ra in vivo, good tolerance for particles in mice. Significant antitumor activity in tumor models in mice. A particularly interesting and unexpected finding was the good uptake in i.p. fat which is of importance since i.p. fat including omentum is ground for metastatic tumor growth (Gerber et al., 2006). One would assume a more lipophilic structure would be required for i.p. fat uptake it was thus a surprise that the calcium carbonate particles used herein would show such a substantial uptake.

Another aspect of the present invention relates to a particle or pharmaceutical composition of the present invention for use as a medicament.

Medical uses of the particles of the present invention includes human or veterinary use in (1) Intracavitary therapy (2) radioembolization (3) radiosynovectomy.

Intracavitary therapy may include treatment of e.g., intraperitonal cancers, intracranial cancers, pleural cancers, bladder cancers, cardiac cancers, cancers in the subarachnoid cavity. Examples of cavities where the particles may be used is cranial cavity, thoracic cavity, lung cavity, spinal cavity, pelvic cavity, pericardium, pleural cavity, bladder cavity or a combination of these including cancers spreading on the peritoneum or meninges and organs within any of these cavities.

In a special embodiment for the use of the particles of the present is treatment or amealeoration of an intracavitary disease which is an infection or inflammation rather than or in combination with cancer.

In one embodiment of the present invention is the infection selected from the group consisting of a bacterial infection and viral infection.

Radioembolization may include treatment of primary or metastatic cancer in an organ e.g., the liver by administering the particles of the present invention to a blood vessel leading to a tumor in the liver or another solid organ infiltrated by tumor tissue.

Radiosynovectomy for joint disorders including chronic inflammations is targeted radiation treatment for painful joint diseases using radioactive substances. Its use includes treatment of hemophilic arthritis.

Today it is based on beta-particle emitting compounds used for inflammatory or rheumatoid diseases, or synovial arthrosis of various joints, in particular of the knee, hand and ankle. The $^{224}$Ra-CC particles described herein which are degradable could be very useful in radiosynovectomy.

The particles are preferably administered by local injection, e.g. intracavitary.

In a special embodiment the particles are injected directly into a tumor.

The articles may be dispersed in various buffers compatible with medical injections, e.g., dissolved salts and or proteins and or lipids and or sugars.

A further aspect of the present invention relates to a particle or pharmaceutical composition of the present invention for use in intracavitary therapy, radioembolization or radiosynovectomy.

Another aspect of the present invention relates to a particle or pharmaceutical composition of the present invention for use in the treatment of cancer.

In one embodiment of the present invention is the cancer selected from the group consisting of intreaperitonial cancers, intracranial cancers, pleural cancers, bladder cancers, cardiac cancers, and cancers in the subarachnoid cavity.

In one embodiment of the present invention is the cancer selected from the group consisting of metastatic cancer, lung cancer, ovarian cancer, colorectal cancer, stomach cancer, pancreatic cancer, breast cancer, neoplastic meningitis, peritoneal cancer, pleural effusion, malignant mesothelioma, breast cancer, sarcomas, brain cancers like glioblastoma and astrocytoma, bladder cancer, and liver cancer.

Another aspect of the present invention relates to a method of treatment or amelioration comprising administration of the particles or the pharmaceutical composition of the present invention to an individual in need thereof.

Methods for Preparations and Kits

Another aspect of the present invention relates to a method for preparing a particle of the present invention, the method comprising bringing an alpha emitting radionuclide and a biodegradable compound in contact with each other with or without using a carrier for the radionuclide.

A solution comprising an alpha emitter, i.e. a $^{224}$Ra solution with progeny $^{212}$Pb in mixture could be pretreated with chelate-antibody conjugate to complex $^{212}$Pb prior to particle labeling to produce a two-component therapeutic system containing a radioimmunoconjugate for $^{212}$Pb antigen-specific treatment and alpha emitter, e.g. $^{224}$Ra-particles for a general cavity treatment.

The preferable way to use this would be by a kit containing a vial A with chelate-conjugated antibody and a vial B with alpha emitter, e.g. $^{224}$Ra in equilibrium with daughter nuclides, and a vial C with microparticles, whereby the content of A is added to vial B, or vice versa, and incubated from a few minutes to a few hours before the mixture is transferred to vial C for further incubation for a few minutes to a few hours before transferring to a syringe and injected into the patient.

This principle could significantly reduce the level of $^{212}$Pb-radioimmunoconjugate needed for therapy since $^{224}$Ra-CC-particles is expected to contribute strongly to the antitumor activity in such a system.

Another aspect of the present invention relates to a kit comprising a nano or micro particle according to the present invention, an alpha emitting radionuclide or a radionuclide generating an alpha emitting daughter, a carrier, diluent and/or excipient, and optionally instructions to use the kit.

Another aspect of the present invention relates to a kit comprising a nano or micro particles according to the present invention, an alpha emitting radionuclide or a radionuclide generating an alpha emitting daughter, a carrier, diluent and/or excipient, and optionally instructions to use the kit to prepare a bifunctional pharmaceutical solution comprising particles suspension and radioimmunoconjugate solution.

In one embodiment of the present invention, the kit comprises a chelator-conjugated molecule, including monoclonal antibody.

The current methods and product allow for centralized production and shipment to the end user since the radionuclide has several days half-life. Another aspect of the presented invention is the use of a biodegradable particle that slowly dissolves into calcium and carbonate thereby producing small amounts of products that are already abundantly present in the body. It is also noteworthy of the following feature: When alpha emitter, e.g. $^{224}$Ra is absorbed on the surface of the calcium carbonate particles, there is a significant release of short living $^{220}$Rn ($t_{1/2}$=56 s) which will together with the ultra-short lived $^{216}$Po ($t_{1/2}$=0.16 s) produce two alpha particles before decaying to the longer lived beta emitter $^{212}$Pb ($t_{1/2}$=10.6 h). Lead has a very high precipitability with calcium carbonate so the $^{212}$Pb in the i.p. fluid will tend to re-associate to the particles diminishing leakage of $^{212}$Pb into the systemic circulation.

It may be of benefit that the $^{220}$Rn, if released from micro particles, is highly lipophilic as e.g., intraperitoneal cancer to a significant degree tends to grow in the omentum, a large fatty pad of tissue that drapes over the intestines in the abdomen (Gerber et al., 2006).

Pre-produced particles and subsequent surface sedimentation or radionuclide co-sedimentation for deeper inclusion of radionuclide are two methods useful for producing a therapeutic product. The first method will allow some release of daughter nuclide $^{220}$Rn which could reduce dose inhomogeneity from inhomogenous particle distribution. Because of the short half life (56 s.) of $^{220}$Rn it will not significantly redistribute from the cavity and not diffuse into deeper layers of the tissue surfaces. Also, the amount of radionuclides are too small to cause any significant physical or chemical effects, e.g., gas pressure, from radon production in the cavity. To some extent it would be beneficial to use larger amounts of particles e.g., a reduced specific activity to improve surface distribution of the radionuclides in the $^{224}$Ra series.

A bifunctional suspension can be made e.g., by the following a $^{224}$Ra solution in pH 5-6 buffer is added TCMC-labeled antibody to 1 mg/ml and incubated from 2 minutes to several hours whereafter the solution is added to a vial with calcium carbonate (CC) particles and incubated for 2 minutes to several hours. The mixture should be administered as soon as possible to avoid reduction of the specific activity of the $^{212}$Pb-labeled product. This will probably best be used as a kit system whereby $^{224}$Ra is in vial A, the chelator conjugated protein is in vial B and CC particles are in vial C.

It may also be possible to add $^{212}$Pb to give an extra strength targeting conjugate in the mixture with $^{224}$Ra-CC particles. Usually, the ratio between $^{224}$Ra and $^{212}$Pb in such a system may be close to 1:1 but in some treatment situations it may be $^{224}$Ra beneficial to increase the amount of $^{212}$Pb-conjugate vs. $^{224}$Ra particles to as much as 10:1 or higher. In the last case it would be required to either add extra $^{212}$Pb before preparation of the targeting conjugate or withdraw some of the $^{224}$Ra-CC particles before the administration of the therapeutic mixture.

The present invention relates to novel radiotherapeutic compounds based on alpha-emitters like $^{224}$Ra with daughter radionuclides. Radium-224 is absorbed onto surfaces of calcium carbonate particles or can be co-sedimented during preparation using carriers e.g., traces of barium sulphate.

In a special embodiment the $^{224}$Ra may be co-crystallized with calcium to form carbonate crystals whereby the $^{224}$Ra is inside the crystals and not on the surface to avoid escape of daughter nuclides.

However, in some settings, a partial slow release of radionuclides may be beneficial as this may effect a better dose homogeneity, e.g., at the surfaces of peritoneum, and the diminishing of radiation "hot spots" from local aggregates of crystal particles.

The radiation range of the major dose component of $^{224}$Ra series, the alpha particles, is typically less than 0.1 mm in tissue allowing the delivery of therapeutically relevant radiation dose levels to the surfaces of the peritoneum and the organs present in the cavity without causing damage to deeper regions of the tissues and peritoneum. It is known from older studies that beta-emitting colloids and particles can show some antitumor activity when used adjuvant in intraperitoneal therapy, but late effects due to radiation of intestines etc. have made these products cost-benefit ratio unfavorable.

The main reason for the side effects is the penetration of radiation in to deeper regions of the intestines due to radiation ranges of several mm. By switching to alpha emitters the problem of irradiating deep below tissue surfaces can be avoided. Another aspect in favor of alpha particles is the high linear energy transfer of the alphas causing a high fraction of lethal double strand breaks on the cells and reducing the effect of oxygen status for cell to survive the treatment. Also the relative biological effectiveness is usually considerably higher for alphas vs. betas.

The current invention is different from previous described alpha-emitting colloids in several ways, (1) it has a slow release of $^{224}$Ra and the daughter nuclide, which may have a dose "smoothening" effect reducing the problems of inhomogeneous distribution of alpha particles in the area of administration. (2) The $^{212}$Pb, which is the longer lived daughter ($t_{1/2}$=10.6 h.) following the decay of the short lived $^{220}$Rn ($t_{1/2}$=56 s.) and $^{216}$Po ($t_{1/2}$=0.15 s.) decay, is easily reabsorbed by the tested particles, which could reduce the leakage of $^{212}$Pb into systemic circulation. Thus it was found that calcium carbonate particles are particularly suitable as carrier for $^{224}$Ra. (3) the particle material itself is non-toxic at the levels used and the particles are slowly degradable to non toxic ions, thereby highly biocompatible.

The particles may be produced in sizes from nanometers to several tens of micrometers and radiolabeled with high labeling yields and can be stored for several days which is important since it allows centralized production and shipment to the hospitals of ready to use particle suspensions. Several different classes of CC crystals may be used including hexagonal β-$CaCO_3$, orthorhombic 2-$CaCO_3$.

General

It should be understood that any feature and/or aspect discussed above in connections with the compounds and particles according to the invention apply by analogy to the methods and applications described herein.

The following figures and examples are provided below to illustrate the present invention. They are intended to be illustrative and are not to be construed as limiting in any way.

EXAMPLES

Example 1

Production of $^{224}$Ra

All work with the concentrated radioactive preparations including evaporation of solvent etc was performed in a glove-box. A source of $^{228}$Th in 1 M $HNO_3$ was acquired from a commercial supplier. Ac-resin was obtained from Eichrom Technologies LLC (Lisle, Ill., USA) in the form of a pre-packed cartridge.

To use smaller volume of solvent, about thirty percent of the materials in a cartridge (Cartridge 1) was extracted and repacked in a smaller column (Cartridge 2) made by a 1 ml filtration column (Isolute SPE, Biotage AB, Uppsala, Sweden). A slurry representing 20% of the original cartridge content was used for immobilizing of $^{228}$Th in 500 microliter 1 M HNO3 which was added 500 microliter of 1 M HCl and incubated by shaking the vial (4 ml vial, E-C sample, Wheaton, Millville, N.J., USA) for at least 4 hours. Cartridge 2 was added a small amount (about 0.1 ml) of the Ac-resin. Thereafter, the slurry was added to cartridge 2 using the prefilled material as a catcher layer. Radium could be eluted from the Cartridge 2 in 2 ml of 1 M HCl. The 2 ml radium solution was evaporated to dryness, using a heater block and flushing the vial with $N_2$ gas through a Teflon tube inlet and outlet in the rubber/Teflon septum on the vial and by leading the acid vapor into a beaker of saturated NaOH by a stream of $N_2$-gas.

The residue was resolved in 0.5 ml 1 M $HNO_3$ and loaded onto a cartridge 3 consisting of a 1 ml Isolute column packed with about 250 mg Dowex anion exchanger. Cartridge 3 was washed with 7 ml 1 M $HNO_3$, which removed $^{212}$Pb, and finally with 3-4 ml 8 M $HNO_3$ to elute $^{224}$Ra. The $^{224}$Ra eluate was evaporated to dryness, using the heater block and a flow of $N_2$-gas, and the residue could be dissolved in 0.1 M HCl. Typically, more than 70% of the $^{224}$Ra present in the $^{228}$Th source could be extracted and purified using the described methods.

Later the anion exchange step was abandoned and the 2 ml crude 1 M HCl was used without evaporation and loaded onto a second Ac resin cartridge which was washed with additional 0.5 ml HCl to produce an eluate of 2.5 ml containing the $^{224}$Ra. This was evaporated into dryness and dissolved in 0.2 ml or more of 0.1 M HCl. Before used in labeling of particles the $^{224}$Ra solution was added an amount corresponding to 10% of the volume with 5 M ammonium acetate to adjust the pH to 5-6.

Example 2

Measurement of Radioactive Samples

Radioactive samples were counted on a Cobra II Autogamma counter (Packard Instruments, Downer Grove, Ill., USA) or a Hidex Automatic Gamma Counter (Hidex, Turku, Finland). During extraction of $^{224}$Ra from the $^{228}$Th source, a CRC-25R dose calibrator (Capintec Inc., Ramsey, N.J., USA) was used.

To determine distribution of $^{224}$Ra, $^{212}$Pb and $^{212}$Bi in real time in samples, a liquid nitrogen cooled high purity germanium (HPGe) detector (GWC6021, Canberra Industries, Meriden Conn., USA) was used. This was combined with a DSA 1000 digital signal analyzer and the Genie 2000 software (Canberra).

Example 3

Preparation of Microparticles

Calcium carbonate microparticles were prepared by a spontaneous precipitation method. A 0.33 M $Na_2CO_3$ (Merck, Germany) solution was rapidly poured into an equal volume of 0.33 M $CaCl_2$ (Merck, Germany). After intense vortexing for 30 seconds, the particle suspension was left for 5 minutes. The particles were filtered off on a filter paper, washed with approximately 30 ml water and dried overnight at room temperature. The filtration and washing was performed in a glass vacuum filtration device (Whatman) with a 0.45 μm nitrocellulose filter (Whatman). Dry microparticles were stored at room temperature. The obtained microparticles were spherical in shape with diameters within 1-10 μm and median 3-5 μm as indicated by microscopy supported by analysis in a Countess™ Automated Cell Counter (Invitrogen).

Example 4

Radiolabeling of Microparticles

A desired amount of $CaCO_3$-particles were transferred to an Eppendorf tube and suspended in 1 ml of water. The particle suspension was sonicated in an ultrasound bath for 10-15 minutes, followed by 4 washing steps; first 2 times with 1 ml of water and then 2 times with 1 ml 0.1M $Na_2SO_4$ (Alfa Aesar, Germany). Particles were separated from the washing solution by centrifugation. After washing, the particles were suspended in DPBS (Gibco, Life Technologies, Carlsbad, Calif., USA) supplemented with 0.5% Bovine Serum Albumin (0.1 ml per 15 mg of particles) and incubated on a HulaMixer (Invitrogen, Life Technologies, Carlsbad, Calif., USA) for 30 minutes at room temperature. The mixing program was as follows: the orbital range of rotation was 14 rpm, the reciprocal range was 20° and the vibration range was 3°. A volume of a 0.1M $Na_2SO_4$ solution corresponding to 3 μg $SO_4$ per mg of particles (0.3%) was added to the particle suspension. Further, $^{224}$Ra-solution was transferred to the tube with the particle suspension, immediately followed by adding 0.07 M $BaCl_2.2H_2O$ (Merck, Germany) solution corresponding to 3 μg Ba per mg of particles (0.3%). Between addition of the different solutions, the particle suspension was thoroughly mixed on a vortex mixer. If the volume to be added of the radioactive and/or BaCl$_2$.2H$_2$O solution exceeded 10 μl, it was added stepwise (5-10 μl at a time, with thorough vortexing in between). The total radiolabeling volume equaled 0.1 ml solution per 15 mg of particles, i.e. the volume of supernatant removed before adding SO$_4$-solution was adjusted according to the volumes of the other solutions to be added. Particles in radiolabeling solution were incubated on a HulaMixer for minimum 1 hour and 30 minutes at room temperature, with the same mixing program as previously described. Finally, the particles were washed from 1-3 times with sucrose buffer. The sucrose buffer contained 94 mg/ml sucrose (Sigma Ultra, St. Louis, Mo., USA) and 2.1 mg/ml Na$_2$SO$_4$. Labeling efficiency was determined by measuring the particles and washing solution(s) with the HPGe detector.

Results: For eight individual experiments, with particles from three different particle batches, the labeling yields were as follows: $^{212}$Pb 96.5±1.9%, $^{212}$Bi 96.7±2.1%, $^{224}$Ra 95.5±3.2% (Mean±SD). The results show that $^{224}$Ra with daughter nuclides are effectively absorbed by the microparticles. Calcium carbonate particles that were stored in powder form at room temperature for 2 months absorbed $^{224}$Ra and its daughter nuclides with similar efficiency as freshly prepared particles.

Example 5

In Vitro Stability of Radiolabeled Microparticles

The in vitro stability of radiolabeled microparticles, prepared as described in Example 4, were studied in 2 different solutions. Particles were incubated in either 1-1.4 ml sucrose buffer at room temperature or 0.5 ml fetal calf serum at 37 gram as previously describes, the suspensions were centrifuged and activities in the supernatant and pelleted particles were measured. Afterwards, if the stability study was to be continued to a later time point, the particle pellet was resuspended in a new aliquot of either sucrose buffer or fetal calf serum and incubated further.

TABLE 2

Retention of $^{224}$Ra by calcium carbonate particles in vitro.

| Solution | Time point | % released activity $^{224}$Ra |
|---|---|---|
| Fetal calf serum | 22 hours | 4.13 ± 3.01% |
|  | 3 days | 1.18 ± 0.69% |
|  | 7 days | 1.76 ± 0.34% |
| Sucrose buffer | 16 hours | 1.07% |
|  | 3 days | 1.70 ± 1.81% |

The data shows that $^{224}$Ra is well retained on the calcium carbonate particles for several days in vitro indicating promising properties for radiotherapeutic use. It also suggest that the product may have a shelf life of several days allowing centralized production and shipment to distant end users.

Example 6

Re-Absorbtion/Association of $^{212}$Pb onto Microparticles

CaCO$_3$ microparticles were prepared as described for the radiolabeling procedure, except no radioactive solution was added. Instead, the particles were incubated in a mix of 450 ction and shipment to distant $^{224}$Ra-solution (pre-heated to 37 r the radiolabeling procedure, except n$^{212}$Pb that absorbed onto d to 37 r the radiolabeling procedure, except no radioactive solution was added. Instead, the particles were incubated in a mix of 450 ction and shipment to distant 10 minutes, the particle suspension was spun down, 250 μl of the supernatant was transferred to an Eppendorf tube and the activity was measured. Afterwards, the particles were resuspended in the supernatant, and the study was extended with measurements after 1 hour and 24 hours. Table 3 presents the results of the study.

TABLE 3

Absorption of $^{212}$Pb from solutions to calcium carbonate particles.

| Time | % of total $^{212}$Pb activity measured in supernatant Canberra germanium detector |
|---|---|
| 0 minutes | 100% |
| 10 minutes | 25.4% |
| 1 hour | 17.9% |
| 24 hours | 29.0% |

The data shows that $^{212}$Pb in the medium is significantly absorbed from the medium indicated that $^{220}$Rn diffusion in the microenvironment of the calcium carbonate particles may be followed by a significant reabsorption of the daughter product $^{212}$Pb. This could reduce systemic toxicity from the uptake of $^{212}$Pb into the blood.

Example 7

In Vivo Biodistribution and Stability of Radiolabeled Microparticles

Background: To evaluate the usefulness of $^{224}$Ra labeled calcium carbonate particles for intracavitary use a particle suspension were injected intraperitoneally in mice and the subsequent biodistribution of $^{224}$Ra was measured. Methods: Radiolabeled microparticles were prepared as described in example 4. After washing, the particle pellet was resuspended in sucrose buffer at pH 7-7.5 to a particle concentration of approximately 13 mg/ml. Institutionally bred, 6-19 weeks old female Athymic Nude-Foxnl$^{nu}$ mice with body weights of 17.1-28.3 g were used for the biodistribution studies. They were administered 0.4 ml particle suspension by intraperitoneal injection, containing 11-18 kBq $^{224}$Ra bound to approximately 5 mg microparticles. The mice were sacrificed and different tissues harvested for radioactivity measurements 20 hours (n=2), 4 days (n=3) and 7 days (n=3) after injection. As a control, biodistribution experiments with free $^{224}$Ra (dissolved RaCl$_2$) were performed, by administering 0.25 ml of 0.9% NaCl solution with approximately 121 (Bq $^{224}$Ra intraperitoneally to each mouse. The $^{224}$RaCl$_2$-solution had a pH of 5.5. For comparison, groups of 3 mice were sacrificed at the same time points after injection as for the biodistribution study with radiolabeled microparticles (FIG. 1A).

Figure 1B:
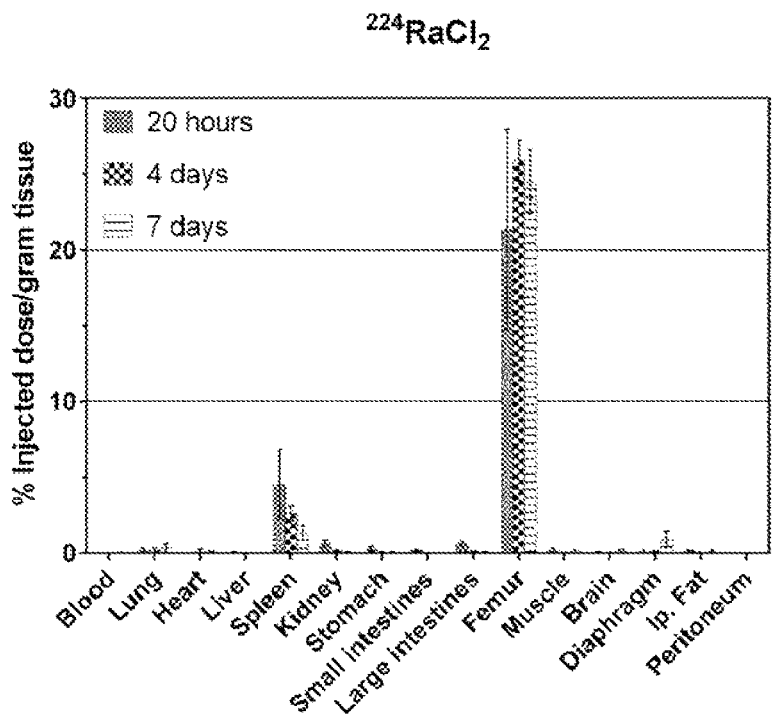

Results: FIGS. 1 A and B show the biodistribution profiles of $^{224}$Ra-labeled calcium carbonate and free $^{224}$Ra respectively. Based on femur uptake the release of $^{224}$Ra is slow from $^{224}$Ra-labeled calcium carbonate with about one fifth after 20 hours increasing to approximately one third at 7 days following administration. This limited release of radionuclide may in one aspect be beneficial since it can reduce dose heterogeneity from the radiolabeled particles. It is noteworthy that there is a considerable uptake in i.p. fat which is promising considering the role of i.p. fat in intraperitoneal spread of cancer metastases. In conclusion, $^{224}$Ra-labeled calcium carbonate has very promising distribution properties regarding intracavitary radiotherapy.

Example 8

Antitumor Activity of $^{224}$Ra-Labeled Microparticles in a Nude Mouse i.p. Cancer Model Background: To test therapeutic activity of $^{224}$Ra-labeled calcium carbonate microparticles a nude mouse tumor model of intraperitoneal micrometastases was used. Materials and methods: SKOV-3-luc cells ($5 \cdot 10^6$ cells in 0.25 ml RPMI) were injected intraperitoneally in institutionally bred, 6 weeks old female Athymic Nude-Foxnl$^{nu}$ mice with body weights of 17.7-23.6 g. Three days later, mice were treated with intraperitoneal injections of $^{224}$Ra-labeled calcium carbonate microparticles in sucrose buffer with activities of 200 kBq/kg (0.25-0.3 ml), 600 kBq/kg (0.35-0.4 ml) or 3 injections of 200 kBq/kg (0.25-0.4 ml). The latter group had 48 hours between each injected fraction. Control animals received saline (0.4 ml) or 200 mg/kg (0.35-0.4 ml) non-labeled microparticles in sucrose buffer. The mice were randomized into treatment groups before cell inoculation, with each group consisting of 8 mice. At day 44 and 45 after treatment start all animals were euthanized by cervical dislocation. During dissection, the presence of macroscopic tumors was assessed by careful visual inspection of each animal and all visible tumors in the peritoneal cavity were removed and weighed.

Figure 2:
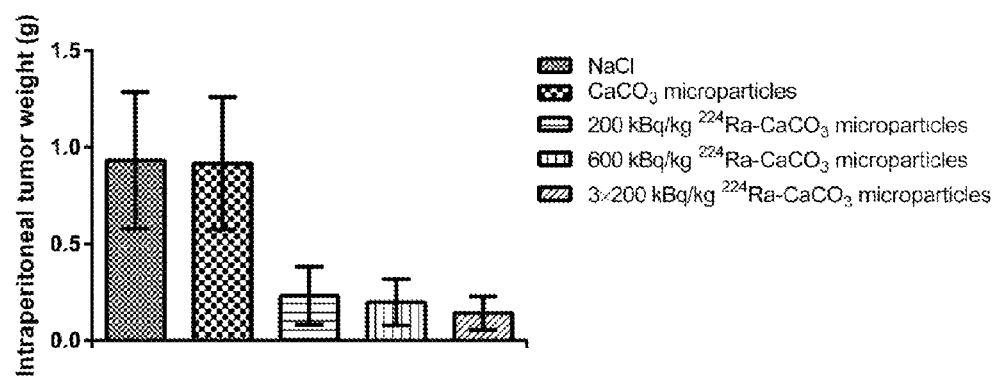
FIG. 2 shows the weight of intraperitoneal SKOV-3 tumors treated with saline, cold particles or $^{224}$Ra-labeled calcium carbonate microparticles on day 44 and 45 after treatment start.

Results: The data are shown in FIG. 2. There was no significant difference between the average tumor weights of the two control groups receiving either saline or non-labeled calcium carbonate microparticles. All groups receiving $^{224}$Ra-labeled microparticles had a strong suppression of tumor growth as shown by the strongly reduced tumor weights that was statistically significant compared to the controls. Although there was no statistically difference between the $^{224}$Ra treatment groups, there was a tendency towards more tumor growth suppression with higher dosage of $^{224}$Ra and fractionated treatment.

In conclusion, $^{224}$Ra labeled calcium carbonate microparticles showed a strong and consistent antitumor activity in mice with intraperitoneal tumors.

Example 9

Therapeutic Effects in an Aggressive Cancer Ascites Model

Background: Human ovarian cancer often leads to intraperiotenal ascites. The human ovarian cancer cell line ES-2 produces aggressive tumor cell growth and cancerous ascites in nude mice.

Materials and methods: ES-2 cells ($10.10^6$ cells in 0.3 ml RPMI) were injected intraperitoneally in institutionally bred, 6 weeks old female Athymic Nude-Foxnl$^{nu}$ mice with body weights of 18.1-23.2 g. 25 hours later, mice were treated with intraperitoneal injections of $^{224}$Ra-labeled calcium carbonate microparticles in sucrose buffer with activities of 100 kBq/kg (0.3 ml), 300 kBq/kg (0.3-0.35 ml) or 500 kBq/kg (0.3-0.35 ml). Control animals received 0.35 ml saline. The mice were randomized into treatment groups before cell inoculation, with each group consisting of 7-8 mice. Animals were weighed and monitored for disease progression minimum 3 times a week, and every day when they displayed clinical signs indicating the approach of final stage of disease. All mice were euthanized by cervical dislocation on the day they reached a loss-of-wellness endpoint, taking into account abdominal distensions that impairs mobility or respiration, rapid loss or gain of body weight together with general animal appearance and behavior. Following euthanasia mice were necropsied for gross pathological examination.

Figure 3:
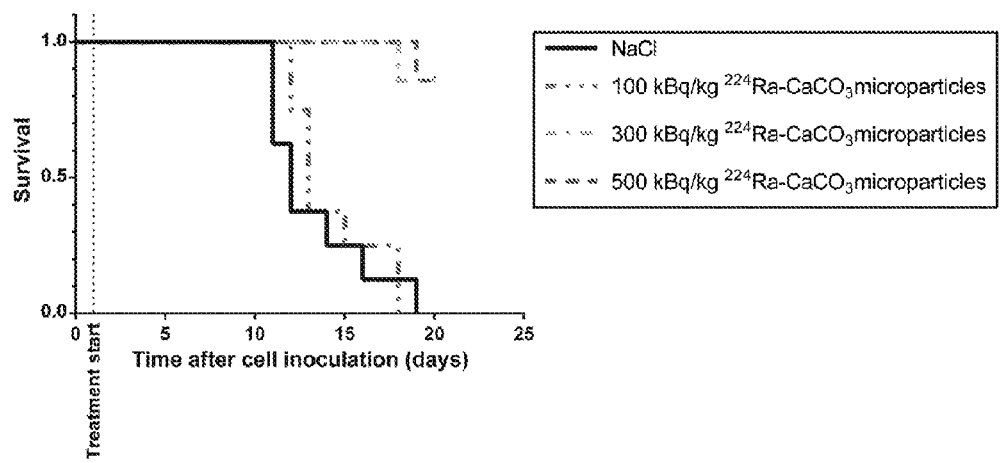
FIG. 3 shows the survival of animals with intraperitoneal ES-2 ascites cancer treated with saline or $^{224}$Ra-labeled calcium carbonate microparticles.

Results: Survival times were recorded as days after tumor cell inoculation, and a preliminary survival curve including data until follow-up day 20 is presented (FIG. 3). At day 19 after tumor cell inoculation, all mice in the saline and lowest dose group (100 kBq/kg) had been euthanized, whereas 86% of the mice (6/7) in the medium (300 kBq/kg) and high (500 kBq/kg) dose group had not reached the study endpoint. These remaining animals were censored at day 20. The median survival of each group is presented in Table 4.

TABLE 4

Median survival of mice with intraperitoneal ES-2 cancer ascites treated with saline or $^{224}$Ra-labeled calcium carbonate.

| Treatment group | Number of mice per group | Median survival time after cell inoculation |
| --- | --- | --- |
| NaCl | 8 | 12 days |
| 100 kBq/kg $^{224}$Ra-CaCO$_3$ microparticles | 8 | 13 days |
| 300 kBq/kg $^{224}$Ra-CaCO$_3$ microparticles | 7 | More than 20 days |
| 500 kBq/kg $^{224}$Ra-CaCO$_3$ microparticles | 7 | More than 20 days |

In conclusion: Considerable disease free life extension was obtained with $^{224}$Ra-labeled calcium carbonate microparticles indicating a significant potential for intracavitary ascites.

Example 10

A Preparation of a Two-Component Radiotherapeutic Mixture

In some aspects it may be beneficial to combine $^{224}$Ra-labeled calcium carbonate particles with a cell specific radiopharmaceutical. This is obtained when a $^{224}$Ra solution in equilibrium with daughter nuclides is combined with a $^{212}$Pb binding chelate conjugate prior to contacting the calcium carbonate particles.

Methods: A 0.2 ml 0.5 M ammonium acetate solution of $^{224}$Ra in equilibrium with daughter nuclides was added 1 mg/ml of TCMC-labeled monoclonal antibody (mAb) (trastuzumab, cetuximab or OI-3) and incubated for 60 minutes. Thereafter the reaction mixture was added to 30 mg of calcium carbonate microparticles in 0.2 ml 1% bovine serum albumin and mixed for 30 minutes. The mixture was thereafter centrifuged and the supernatant and pellet was counted separately on a gamma counter and analysed with a germanium detector.

A radiotherapeutic mixture consisting of $^{212}$Pb-labeled antibody and $^{224}$Ra-CaCO3 microparticles was prepared. For labeling antibody with $^{212}$Pb, the antibody Cetuximab was first conjugated to a chelator, TCMC.

To prepare the radioimmunoconjugate, $^{224}$Ra-solution with 0.5 M ammonium acetate (pH between 5 and 6) was mixed with TCMC-Cetuximab and reacted for 30 minutes at 37° C. with a rotation rate of 350 rpm. The radiochemical purity of the resulting product was evaluated with chromatography strips (Biodex), and was found to be above 95% for $^{212}$Pb. CaCO3 microparticles were prepared as described for the radiolabeling procedure, except that the radioactivity added was the solution described above, containing both free $^{224}$Ra and $^{212}$Pb-labeled TCMC-Cetuximab. After 1.5 hours incubation at room temperature on a HulaMixer, the particles in radiolabeling solution were spun down and the supernatant and particle fraction separated. The activity distribution of $^{224}$Ra and $^{212}$Pb in the particle pellet and the supernatant was determined with the HPGe detector. A radiochemical purity analysis was performed on an aliquot of the supernatant.

Data are presented in Tables 5 and 6. Table 6 shows that 66.39% of the total $^{212}$Pb activity was found in the supernatant, while 98.41% of the $^{224}$Ra was retained on the particles. Of the released $^{212}$Pb at least 98% was protein bound (Table 5), which represents the fraction of antibody bound $^{212}$Pb before the antibody was mixed with the particles. In Table 6 the fraction of $^{212}$Pb-antibody conjugate and $^{224}$Ra in free circulation and bound to the calcium carbonate particles is presented. The data shows that $^{224}$Ra binds to the particles while the major part of the $^{212}$Pb-conjugate is free to circulate in the medium. Thus a bifunctional radiotherapeutic mixture suitable for injection was obtained.

In conclusion, $^{224}$Ra solutions mixed with $^{212}$Pb-TCMC-antibody conjugates can be used to prepare $^{224}$Ra-CC microparticles yielding a two component therapeutic mixture with radioimmunoconjugate (RIC) and radiolabeled microparticles with antigen-targeting properties as well as microparticle radiotherapeutic properties. This may be advantageous in producing a combination of general cavity irradiation and a specific tumor cell targeting RIC treatment against cancer. The addition of RIC may enhance the microdistribution of alpha radiation to improve therapeutic effect on resistant cancer cells.

TABLE 5

Thin layer chromatography analyses of $^{212}$Pb-TCMC-antibody conjugate before and after absorption to calcium carbonate particles. RCP analyses of protein bound fraction

| | Time in formulation buffer | Canberra germanium detector gamma spectroscopy $^{212}$Pb | Cobra II NaI gamma counter 70-80 keV | 220-260 keV |
|---|---|---|---|---|
| Before mixing with particles | 13 minutes | 98,2% | 97.2% | 95.2% |
| | 20 minutes | | 99.6% | 98.1% |
| After particle labeling | 10 minutes | | 100.0% | 98.1% |
| | 20 minutes | 98.2% | | 100.0% |

TABLE 6

Particle absorption of $^{224}$Ra solution containing $^{212}$Pb-TCMC-antibody

| | % of total activity | |
|---|---|---|
| | $^{212}$Pb | $^{224}$Ra |
| Particles | 33.61% | 98.41% |
| Supernatant/antibody fraction | 66.39% | 1.59% |

Example 10 B

Description of a Kit System for Preparing a $^{212}$Pb Radioimmunoconjugate and $^{224}$Ra Microparticle Radiotherapeutic Mixture A vial (A) with solution of $^{224}$Ra in an aqueous solution (e.g. 0.5 M ammonium acetate, pH 5-6) is left to decay for 1 day or more for producing $^{212}$Pb. An aqueous solution (B) of TCMC-antibody conjugate or similar chelate conjugated antibody and a vial (C) with dry or aqueous calcium carbonate microparticles. The contents of vial A and B are mixed together in one of the vials and incubated for 1 min to 4 hours and thereafter mixed with vial C and incubated for 1 minute to 4 hours. After each steps of incubation a quality control may or may not be performed. Finally the combined mixture of A, B, and C is drawn into a syringe and administered to a patient.

REFERENCES

Atcher R W and Hines JJ. Colloid labelled with radionuclide and method
U.S. Pat. No. 4,970,062 A (submitted 1989)
Bloomer, W. D., McLaughlin, W. H., Neirinckx, R. D., Adelstein, S. J., Gordon, P. R., Ruth,
T. J., Wolf, A. P. Astatine-211-tellurium radiocolloid cures experimental malignant ascites. Science. 1981; 212:340-341.
Boudousq V1, Bobyk L, Busson M, Garambois V, Jarlier M, Charalambatou P, Pelegrin A, Paillas S, Chouin N, Quenet F, Maquaire P, Torgue J, Navarro-Teulon I, Pouget JP. Comparison between internalizing anti-HER2 mAbs and non-internalizing anti-CEA mAbs in alpha-radioimmunotherapy of small volume peritoneal carcinomatosis using 212Pb. PLoS One. 2013 Jul. 29; 8(7).
Gustafsson AM1, Back T, Elgqvist J, Jacobsson L, Hultborn R, Albertsson P, Morgenstern A, Bruchertseifer F, Jensen H, Lindegren S. Comparison of therapeutic efficacy and biodistribution of 213Bi- and 211At-labeled monoclonal antibody MX35 in an ovarian cancer model. Nucl Med Biol. 2012 January; 39(1):15-22.
Kirby, H. W; Salutsky, Murrell L (1964). The Radiochemistry of Radium (PDF). National Academies Press, pp 5.
Larsen RH and Salberg G. Alpha-emitting hydroxyapatite particles.
U.S. Pat. No. 8,142,758 B2 (submitted 2005)
Liu S. Bifunctional coupling agents for radiolabeling of biomolecules and target specific delivery of metallic radionuclides. Adv Drug Deliv Rev. 2008, 60 (12), 1347-1370.
Ritter M A, Cleaver J E, Tobias C A. High-LET radiations induce a large proportion of non-rejoining DNA breaks. Nature. 1977 Apr. 14; 266(5603):653-5. Scott A. Gerber,*

Viktoriya Y. Rybalko,* Chad E. Bigelow, † Amit A. Lugade,* Thomas H. Foster, † John G. Frelinger,* and Edith M. Lord* Preferential Attachment of Peritoneal Tumor Metastases to Omental Immune Aggregates and Possible Role of a Unique Vascular Microenvironment in Metastatic Survival and Growth. Am J Pathol. 2006 November; 169(5): 1739-1752.

Vergote I, Larsen RH, de Vos L, Nesland J M, Bruland O, Bjørgum J, Alstad J, Trope C, Nustad K. Therapeutic efficacy of the alpha-emitter 211At bound on microspheres compared with 90Y and 32P colloids in a murine intraperitoneal tumor model. Gynecol Oncol. 1992 December; 47(3):366-72.

ITEMS OF THE INVENTION

1. A particle comprising a degradable compound and an alpha emitting radionuclide and/or a radionuclide generating alpha emitting daughter.
2. The particle according to item 1, wherein the radionuclide is selected from the group consisting of $^{224}$Ra, $^{212}$Bi, $^{212}$Pb $^{223}$Ra, $^{225}$Ra, $^{225}$Ac, $^{213}$Bi, $^{211}$At, $^{227}$Th.
3. The particle according to anyone of items 1-2, wherein the degradable compound is selected from the group consisting of $CaCO_3$, PEG modified $CaCO_3$, protein modified $CaCO_3$, carbohydrate modified $CaCO_3$, lipid modified $CaCO_3$, vitamin modified $CaCO_3$, organic compound modified $CaCO_3$, polymer modified $CaCO_3$ and/or inorganic crystal modified $CaCO_3$.
4. The particle according to anyone of items 1-3, wherein size of the particle is from 1 nm to 500 μm.
5. The particle according to anyone of items 1-4, further comprising one or more compounds selected from the group consisting of a monoclonal antibody, a polyclonal antibody, a radioimmunoconjugate, an immunoconjugate, a chelate antibody conjugate, vitamins including folate and folate derivatives, peptides, minibodies, and affibodies.
6. A pharmaceutical composition comprising one or more particles according to anyone of items 1-5 and a diluent, carrier, surfactant, and/or excipient.
7. The pharmaceutical composition according to item 6, prepared with an amount of radionuclide that is 1 kBq to 10 GBq per dosing.
8. The pharmaceutical composition according to anyone of items 6-7, prepared with an amount of radionuclide that is 50 MBq to 100 GBq suitable for multidose industrial scale production.
9. The pharmaceutical composition according to anyone of items 6-8, wherein the composition is a particle suspension comprising monodisperse or polydisperse particles labeled with an alpha emitting radionuclide and/or a radionuclide generating alpha emitting daughter.
10. The pharmaceutical composition according to anyone of items 6-9, which is suitable for intravenous or intracavitary injection.
11. The particle according to anyone of items 1-5 or the pharmaceutical composition according to items 6-9, for use as a medicament.
12. The particle according to anyone of items 1-5 or the pharmaceutical composition according to items 6-9, for use is intracavitary therapy, radioembolization or radiosynovectomy.
13. The particle according to anyone of items 1-5 or the pharmaceutical composition according to items 6-9, for use in the treatment of cancer.
14. The particle according to anyone of items 1-5 or the pharmaceutical composition according to items 6-9, for use according to item 12-13, wherein the cancer is selected from the group consisting of intreaperitonial cancers, intracranial cancers, pleural cancers, bladder cancers, cardiac cancers, and cancers in the subarachnoid cavity.
15. A method of treatment or amelioration comprising administration of the particles according to anyone of items 1-5 or the pharmaceutical composition according to item 6-9 to an individual in need thereof using single treatment or repeated dosing.
16. A method for preparing a particle according to anyone of items 1-6, the method comprising bringing an alpha emitting radionuclide and a biodegradable compound in contact with each other with or without using a carrier for the radionuclide.
17. A kit comprising;
   a nano or micro particle according to anyone of items 1-6,
   an alpha emitting radionuclide or a radionuclide generating an alpha emitting daughter.
   a carrier, diluent and/or excipient, and
   optionally instructions to use the kit.
18. A kit comprising;
   a nano or micro particles according to anyone of items 1-6,
   an alpha emitting radionuclide or a radionuclide generating an alpha emitting daughter,
   a carrier, diluent and/or excipient, and
   optionally instructions to use the kit to prepare a bifunctional pharmaceutical solution comprising particles suspension and radioimmunoconjugate solution.
19. A kit according to item 18, further comprising a chelator-conjugated molecule, including monoclonal antibody.

What is claimed is:

1. A therapeutic particle comprising:
   a degradable compound comprising $CaCO_3$; and
   an alpha emitting $^{224}$Ra radionuclide; and
   daughter radionuclides of the alpha emitting $^{224}$Ra radionuclide, wherein the daughter radionuclides are $^{220}$Rn, $^{216}$Po, and $^{212}$Pb.

2. The therapeutic particle according to claim 1, wherein the therapeutic particle has a size between 1 nm to 500 μm.

3. The therapeutic particle according to claim 1, further comprising one or more compounds selected from the group consisting of a monoclonal antibody, a polyclonal antibody, a radioimmunoconjugate, an immunoconjugate, a chelate antibody conjugate, vitamins including folate and folate derivatives, peptides, minibodies, and affibodies.

4. A pharmaceutical composition comprising:
   one or more therapeutic particles according to claim 1; and
   a diluent, carrier, surfactant, and/or excipient.

5. The pharmaceutical composition according to claim 4, wherein the pharmaceutical composition is prepared with an amount of the alpha emitting $^{224}$Ra radionuclide that is 1 kBq to 10 GBq per dosing or with an amount of the alpha emitting $^{224}$Ra radionuclide that is 50 MBq to 100 GBq suitable for multidose industrial scale production.

6. The pharmaceutical composition according to claim 4, wherein the one or more therapeutic particles are monodisperse or polydisperse, and form a particle suspension.

7. The pharmaceutical composition according to claim 4, wherein the pharmaceutical composition is formulated for intravenous or intracavitary injection.

8. A method of treating cancer in a human in need thereof, comprising administering to the human one or more therapeutic particles, wherein the one or more particles comprise:
   a degradable compound comprising $CaCO_3$; and
   an alpha emitting $^{224}$Ra radionuclide; and daughter radionuclides of the alpha emitting $^{224}$Ra radionuclide, wherein the daughter radionuclides are $^{220}$Rn, $^{216}$Po, and $^{212}$Pb.

9. The method according to claim 8, wherein the method is an intracavitary therapy, radioembolization or radiosynovectomy.

10. The method according to claim 8, wherein the cancer is selected from the group consisting of intreaperitonial cancers, intracranial cancers, pleural cancers, bladder cancers, cardiac cancers, and any cancer in the subarachnoid cavity.

11. A kit comprising;
a therapeutic particle according to claim 1;
a carrier, diluent and/or excipient; and
instructions for use of the particle in treating cancer.

* * * * *